(12) United States Patent
Glenn et al.

(10) Patent No.: US 6,833,435 B2
(45) Date of Patent: Dec. 21, 2004

(54) COMPOSITIONS ISOLATED FROM BOVINE TISSUES AND METHODS FOR THEIR USE

(76) Inventors: Matthew Glenn, 14 Waimarie Road, Auckland (NZ); Murray R. Grigor, 34D Sayegh Street, Auckland (NZ); Adrian J. Molenaar, 1 Wilson Street, Hamilton (NZ); Stephen R. Davis, 124 Rosebank Drive, RD3, Hamilton (NZ)

(*) Notice: Subject to any disclaimer, the term of this patent is extended or adjusted under 35 U.S.C. 154(b) by 0 days.

(21) Appl. No.: 10/079,754

(22) Filed: Feb. 19, 2002

(65) Prior Publication Data

US 2002/0164625 A1 Nov. 7, 2002

Related U.S. Application Data

(63) Continuation-in-part of application No. 09/699,146, filed on Oct. 27, 2000, now abandoned, and a continuation-in-part of application No. 09/644,190, filed on Aug. 22, 2000, now abandoned.
(60) Provisional application No. 60/162,701, filed on Oct. 29, 1999, and provisional application No. 60/150,330, filed on Aug. 23, 1999.

(51) Int. Cl.[7] ............................................. A61K 38/17
(52) U.S. Cl. ....................... 530/324; 514/12; 424/185.1
(58) Field of Search ........................... 530/324; 504/12; 424/185.1

(56) References Cited

U.S. PATENT DOCUMENTS

| | | | |
|---|---|---|---|
| 5,486,503 A | 1/1996 | Oppenheim et al. | 514/2 |
| 5,631,228 A | 5/1997 | Oppenheim et al. | 514/12 |
| 5,646,119 A | 7/1997 | Oppenheim et al. | 514/12 |
| 5,672,351 A | 9/1997 | Chikindas et al. | 424/401 |
| 5,696,078 A | 12/1997 | Oppenheim et al. | 514/2 |
| 5,885,965 A | 3/1999 | Oppenheim et al. | 514/12 |
| 5,912,230 A | 6/1999 | Oppenheim et al. | 514/12 |
| 6,004,944 A | 12/1999 | Rothman et al. | 514/44 |

FOREIGN PATENT DOCUMENTS

| | | | |
|---|---|---|---|
| WO | 9640768 | 12/1996 | C07K/14/47 |
| WO | 0024779 | 5/2000 | C07K/14/81 |

*Primary Examiner*—James Martinell
(74) *Attorney, Agent, or Firm*—Ann W. Speckman; Janet Sleath; Susan J. Friedman

(57) ABSTRACT

Isolated polynucleotides encoding histatin polypeptides expressed in bovine tissues, including mammary gland and paratoid salivary gland tissues, are provided, together with genetic constructs and host cells comprising such isolated polynucleotides. Methods for the use of such polynucleotides and polypeptides are also provided.

7 Claims, No Drawings

SEQUENCE LISTING

<160> NUMBER OF SEQ ID NOS: 15

<210> SEQ ID NO 1
<211> LENGTH: 505
<212> TYPE: DNA
<213> ORGANISM: Bovine

<400> SEQUENCE: 1

```
ttgaagatga catcaggtac cgctgtccag gactccacca aatatgaaga tctttatctt      60
tgtcttcatt atggctctca tcctagccat gattagagct gattcatctg aagagaaacg     120
tcacaggaaa cggaaaaaac atcatagagg atattttcaa caataccagc catatcaacg     180
atatccacta aattatcctc ctgcgtatcc atttccttaa aatgctgctt agtaactaca     240
ggacatgatt agagagattt ttcacaatga ttttttcctac tctttctgtt gtgttgaaaa     300
ccatctttca aatgaataaa acaaagaaaa aaaaatcagt caagtagttg cacaacacat     360
acttggaatc aaatatcaat attttaaaac ataataatga tagtctctga actatgtaat     420
tggtttctac tttcttttct ctgtcactta ccatgcatgc ttaataaatt gatctatcaa     480
gcataaaaaa aaaaaaaaaa aaaaa                                           505
```

<210> SEQ ID NO 2
<211> LENGTH: 585
<212> TYPE: DNA
<213> ORGANISM: Bovine

<400> SEQUENCE: 2

```
atggattcga ttggaccaga aaagtggtaa aatcttgatc aaagaaatcc ttaacaatat      60
actaaagaaa gaagcttgtc caagggaaaa ttaaaaagcc agcaattgaa gatgacatca     120
ggtaccgctg tccaggactc caccaaatat gaagatcttt atctttatct tcattatggc     180
tctcatccta gccatgatta gagctgattc atctgaagag aaacgtcaca ggaaacggaa     240
aaaacatcat agaggatatt ttcaacaata ccagccatat caacgatatc cactaaatta     300
```

```
tcctcctgcg tatccatttc cttaaaatgc tgcttagtaa ctacaggaca tgattagaga    360 gattttcac aatgattttt cctactcttt ctgttgtgtt gaaaaccatc tttcaaatga     420
ataaaacaaa gaaaaaaaaa tcagtcaagt agttgcacaa cacatacttg aatcaaata    480 tcaatatttt aaaacataat aatgacagtc tctgaactat gtaattggtt tctactttct   540
tttctctgtc acttaccatg catgcttaat aaattgatct atcaa                    585
```

<210> SEQ ID NO 3
<211> LENGTH: 869
<212> TYPE: DNA
<213> ORGANISM: Bovine

<400> SEQUENCE: 3

```
gtccaaggga aaattaaaaa gccagcaatt gaagatgaca tcaggtaccg ctgtccagga   60
ctccaccaaa tatgaagatc tttatcttta tcttcattat ggctctcatc ctagccatga  120
ttagagctga ttcatctgaa gagaaacgtc acaggaaacg gaaaaaacat catgtatgta   180
ttcctctgat aatgtggtat agtataagaa tattttttac tcagaatatt tattctataa  240
gagaatacat atttatcttt gaaatatatc tatacaatga ttagcttatg tgtccattga  300
attatctttt tatgatacac taggtaaaga ccccaaagac ttgtgtgctg ttactgttta  360
catagaaacc tataatgcca ccctgataaa gccagttatt ttctaagaaa agttatttct  420
gtttggtaaa taattgcctt cctctgaaga atactgaaat tctaattata ctaagtacaa   480
tatacaccta aaggaccata gaggctgcta aagaacatat attatgtggt cagtttccat   540
tttctgattt cttttgggag gtaatgtatg ttaattgacc aagttaaaga agagagacaa   600
tttcatttat ttaacatttt tcttaatgat atgtatcact ggtgtctcat attatttga   660 catgtctaat caggttgata ggtctccaga attcttacta atacagtaag tactgctact  720
gctactgcta agttgcttca gtcatgtcca actctgtgcg accccataga cagcagcgca   780
ccaggctccc ctgcccctgg gattctccag gcaaggatac tggagtgggt tgccatttca   840
gataaattca aatagcttca aaaaaaaaa                                      869
```

<210> SEQ ID NO 4
<211> LENGTH: 604
<212> TYPE: DNA
<213> ORGANISM: Bovine

<400> SEQUENCE: 4

```
gaagtatttt cagttctata ataagatctc ataactgatg taattacaaa acaaatgaa    60 ggatttcaag gtatttaaac acagcagttt tctagcaaag aacatctcct gaagcatcag   120
aatttcatct ttcatgactg gactccacca aatatgaaga tctttatctt tgtcttcatt   180
atggctctca tcctagccat gattagagct gattcatctg aagagaaacg tcacaggaaa   240
cggaaaaaac atcatagagg atattttcaa caataccagc catatcaacg atatccacta   300
aattatcctc ctgcgtatcc atttccttaa aatgctgctt agtaactaca ggacatgatt   360
agagagattt ttcacaatga ttttcctac tctttctgtt gtgttgaaaa ccatctttca    420
aatgaataaa acaagaaaaa aaaaatcagt caagtagttg cacaacacat acttggaatc    480
aaatatcaat attttaaaac ataataatga tagtctctga actatgtaat ggtttctac    540 tttctttttct ctgtcactta ccatgcatgc ttaataaatt gatctatcaa gcataaaaaa  600
aaaa                                                                 604
```

```
<210> SEQ ID NO 5
<211> LENGTH: 96
<212> TYPE: DNA
<213> ORGANISM: Bovine

<400> SEQUENCE: 5
tttcaacaat accagccata tgaacgatat ccactaaatt atcctcctgc gtatccatta      60
tcttaaaatg ctgcttacca actacaggac atgata                               96

<210> SEQ ID NO 6
<211> LENGTH: 525
<212> TYPE: DNA
<213> ORGANISM: Bovine

<400> SEQUENCE: 6
tgaagatgac atcaggtacc gctgtccagg actccaccaa atatgaagat ctttatcttt      60
gtcttcatta tggctctcat cctagccatg attagagctg attcatctga agagaaacgt     120
cacaggaaac ggaaaaaaca tcatgttgat aggtctccag aattcttact aatacaagag     180
gatattttca acaataccag ccatatcaac gatatccact aaattatcct cctgcgtatc     240
catttcctta aaatgctgct tagtaactac aggacatgat tagagagatt tttcacaatg     300
atttttccta ctctttctgt tgtgttgaaa accatctttc aaatgaataa acaaagaaa      360 aaaaaatcag tcaagtagtt gcacaacaca tacttggaat caaatatcaa tattttaaaa     420
cataataatg atagtctctg aactatgtaa ttggtttcta ctttcttttc tctgtcactt     480
accatgcatg cttaataaat tgatctatca agcataaaaa aaaaa                     525

<210> SEQ ID NO 7
<211> LENGTH: 58
<212> TYPE: PRT
<213> ORGANISM: Bovine

<400> SEQUENCE: 7

Met Lys Ile Phe Ile Phe Val Phe Ile Met Ala Leu Ile Leu Ala Met
 1               5                  10                  15

Ile Arg Ala Asp Ser Ser Glu Glu Lys Arg His Arg Lys Arg Lys Lys
                20                  25                  30

His His Arg Gly Tyr Phe Gln Gln Tyr Gln Pro Tyr Gln Arg Tyr Pro
            35                  40                  45

Leu Asn Tyr Pro Pro Ala Tyr Pro Phe Pro
        50                  55

<210> SEQ ID NO 8
<211> LENGTH: 58
<212> TYPE: PRT
<213> ORGANISM: Bovine

<400> SEQUENCE: 8

Met Lys Ile Phe Ile Phe Ile Phe Ile Met Ala Leu Ile Leu Ala Met
 1               5                  10                  15

Ile Arg Ala Asp Ser Ser Glu Glu Lys Arg His Arg Lys Arg Lys Lys
                20                  25                  30

His His Arg Gly Tyr Phe Gln Gln Tyr Gln Pro Tyr Gln Arg Tyr Pro
            35                  40                  45

Leu Asn Tyr Pro Pro Ala Tyr Pro Phe Pro
        50                  55
```

<210> SEQ ID NO 9
<211> LENGTH: 70
<212> TYPE: PRT
<213> ORGANISM: Bovine

<400> SEQUENCE: 9

Met Lys Ile Phe Ile Phe Ile Phe Ile Met Ala Leu Ile Leu Ala Met
1               5                   10                  15

Ile Arg Ala Asp Ser Ser Glu Glu Lys Arg His Arg Lys Arg Lys Lys
            20                  25                  30

His His Val Cys Ile Pro Leu Ile Met Trp Tyr Ser Ile Arg Ile Phe
        35                  40                  45

Phe Thr Gln Asn Ile Tyr Ser Ile Arg Glu Tyr Ile Phe Ile Phe Glu
    50                  55                  60

Ile Tyr Leu Tyr Asn Asp
65                  70

<210> SEQ ID NO 10
<211> LENGTH: 58
<212> TYPE: PRT
<213> ORGANISM: Bovine

<400> SEQUENCE: 10

Met Lys Ile Phe Ile Phe Val Phe Ile Met Ala Leu Ile Leu Ala Met
1               5                   10                  15

Ile Arg Ala Asp Ser Ser Glu Glu Lys Arg His Arg Lys Arg Lys Lys
            20                  25                  30

His His Arg Gly Tyr Phe Gln Gln Tyr Gln Pro Tyr Gln Arg Tyr Pro
        35                  40                  45

Leu Asn Tyr Pro Pro Ala Tyr Pro Phe Pro
    50                  55

<210> SEQ ID NO 11
<211> LENGTH: 21
<212> TYPE: PRT
<213> ORGANISM: Bovine

<400> SEQUENCE: 11

Phe Gln Gln Tyr Gln Pro Tyr Glu Arg Tyr Pro Leu Asn Tyr Pro Pro
1               5                   10                  15

Ala Tyr Pro Leu Ser
            20

<210> SEQ ID NO 12
<211> LENGTH: 59
<212> TYPE: PRT
<213> ORGANISM: Bovine

<400> SEQUENCE: 12

Met Lys Ile Phe Ile Phe Val Phe Ile Met Ala Leu Ile Leu Ala Met
1               5                   10                  15

Ile Arg Ala Asp Ser Ser Glu Glu Lys Arg His Arg Lys Arg Lys Lys
            20                  25                  30

His His Val Asp Arg Ser Pro Glu Phe Leu Leu Ile Gln Glu Asp Ile
        35                  40                  45

Phe Asn Asn Thr Ser His Ile Asn Asp Ile His
    50                  55

<210> SEQ ID NO 13
<211> LENGTH: 8

```
<212> TYPE: PRT
<213> ORGANISM: Artificial Sequence
<220> FEATURE:
<223> OTHER INFORMATION: Made in a lab from synthetic material
<220> FEATURE:
<221> NAME/KEY: VARIANT
<222> LOCATION: (1)...(8)
<223> OTHER INFORMATION: Xaa = Any Amino Acid

<400> SEQUENCE: 13

Xaa Xaa His His Xaa Xaa Tyr Xaa
 1               5

<210> SEQ ID NO 14
<211> LENGTH: 8
<212> TYPE: PRT
<213> ORGANISM: Artificial Sequence
<220> FEATURE:
<223> OTHER INFORMATION: Made in a lab from synthetic material

<400> SEQUENCE: 14

Lys Lys His His Arg Lys Tyr Phe
 1               5

<210> SEQ ID NO 15
<211> LENGTH: 267
<212> TYPE: DNA
<213> ORGANISM: Bovine

<400> SEQUENCE: 15
ttgaagatga catcaggtac cgctgtccag gactccacca aatatgaaga tctttatctt      60
tgtcttcatt atggctctca tcctagccat gattagagct gattcatctg aagagaaacg     120
tcacaggaaa cggaaaaaac atcatagagg atattttcaa caataccagc catatcaacg     180
atatccacta aattatcctc ctgcgtatcc atttccttaa aatgctgctt agtaactaca     240
ggacatgatt agagagattt ttcacaa                                          267
```

COMPOSITIONS ISOLATED FROM BOVINE TISSUES AND METHODS FOR THEIR USE

CROSS-REFERENCE TO RELATED APPLICATIONS

This application is a continuation-in-part of U.S. patent application Ser. No. 09/699,146, filed Oct. 27, 2000, now abandoned, which claims priority to U.S. Provisional Patent Application No. 60/162,701, filed Oct. 29, 1999; and is a continuation-in-part of U.S. patent application Ser. No. 09/644,190, filed Aug. 22, 2000, now abandoned, which claims priority to U.S. Provisional Patent Application No. 60/150,330, filed Aug. 23, 1999.

TECHNICAL FIELD OF THE INVENTION

This invention relates generally to polypeptides expressed in bovine tissues, including mammary gland cells and paratoid salivary gland cells, to polynucleotides encoding such polypeptides, and to methods for treating a mammal involving administration of a polypeptide or polynucleotide of the present invention. More particularly, the present invention relates to polynucleotides that encode or statherins and/or histatins, together with polypeptides encoded by such polynucleotides and methods for the use of such polypeptides and polynucleotides.

BACKGROUND OF THE INVENTION

Human histatins are a family of low molecular weight (51–77 amino acids), neutral to very basic, histidine-rich, proteins that are specific to salivary secretions. Histatins are believed to function as part of the non-immune defense system, particularly in the oral cavity. Salivary histatins have been shown to be potent antifungal, antimicrobial and anti-bacterial agents, and to have promise as therapeutic agents in humans with oral candidosis (Tsai et al. *Infection and Immunity* 64:5000–5007, 1996). In particular, histatins have been shown to kill the pathogenic yeast, *Candida albicans* (Oppenheim et al. *J. Biol. Chem.* 263:7472–7477, 1988), with peptides representing defined portions of the amino acid sequences of naturally occurring human and macaque histatin being shown to have superior anti-candidal activity over the intact native histatin (Zuo et al. *Gene* 161:87–91, 1995; U.S. Pat. No. 5,486,503).

Human statherin is a low molecular weight, acidic phosphoprotein that acts to inhibit precipitation of calcium phosphate salts in the oral cavity, and which is believed to belong to the same gene family as human histatins (Sabatini et al. *Mol. Biol. Evol.* 10:497–511, 1993).

Fungal and bacterial infections are common and can be life threatening in patients with compromised immune systems. Candidal infections often occur in diabetics, during pregnancy and following medication with antibiotics, steroid hormones or oral contraceptives. Oral candidiasis is common in patients infected with HIV, as well as in cancer patients following treatment with radiation or chemotherapy. Systemic fungal infections in immuno-compromised patients and in patients in intensive care are often fatal since there are few effective anti-fungal treatments for intravenous administration. Similarly, bacterial infections can lead to severe disease and even death. Although several anti-fungal and ant-bacterial agents are available, these agents are not completely effective, with many not being appropriate for oral or systemic administration. Thus there remains a need in the art for preparations have effective anti-fungal and anti-bacterial properties.

SUMMARY OF THE INVENTION

The present invention provides isolated histatin-like polypeptides expressed in bovine tissues and isolated polynucleotides encoding such polypeptides, together with genetic constructs and host cells comprising such polynucleotides. Methods for using such polypeptides, polynucleotides and genetic constructs are also provided.

In specific embodiments, isolated polynucleotides are provided that comprise a polynucleotide sequence selected from the group consisting of: (a) sequences recited in SEQ ID NOS: 1–6; (b) complements of the sequences recited in SEQ ID NOS: 1–6; (c) reverse complements of the sequences recited in SEQ ID NOS: 1–6; (d) reverse sequences of the sequences recited in SEQ ID NOS: 1–6; and (e) sequences having at least 75%, 90% or 95% identity to a sequence of (a)–(d), the percentage identity being determined as described below. Polynucleotides comprising at least a specified number of contiguous residues ("x-mers") of any of the sequences identified as SEQ ID NOS: 1–6 are also provided, together with extended sequences, and oligonucleotide probes and primers corresponding to the sequences set out in SEQ ID NOS: 1–6. All of these polynucleotides and oligonucleotide probes and primers are collectively referred to herein as "polynucleotides of the present invention".

In further embodiments, the present invention provides isolated polypeptides comprising an amino acid sequence encoded by a polynucleotide selected from the group consisting of: (a) sequences provided in SEQ ID NOS: 1–6; and (b) sequences having at least 75%, 90% or 95% identity to a sequence provided in SEQ ID NOS: 1–6. In specific embodiments, such polypeptides comprise a sequence selected from the group consisting of sequences identified as SEQ ID NO: 7–12, and variants thereof. The present invention further provides isolated polypeptides comprising at least a functional portion of an amino acid sequence encoded by a polynucleotide selected from the group consisting of: (a) sequences provided in SEQ ID NOS: 1–6; and (b) sequences having 75%, 90% or 95% identity to a sequence of SEQ ID NOS: 1–6.

In related embodiments, the present invention provides genetic constructs comprising the inventive polynucleotides, together with host cells transformed with such constructs, and organisms comprising such host cells.

In a further aspect, the present invention provides compositions comprising an inventive polypeptide or polynucleotides in combination with a physiologically acceptable carrier and/or an immunostimulant, together with methods for the use of such compositions in the treatment of a disorder in a mammal, such as a cow or a human. Preferably the disorder is selected from the group consisting of bacterial, microbial and fungal infections. Such infections may be either local or systemic. In certain embodiments, anti-microbial cosmetic compositions comprising the inventive polypeptides are provided.

The isolated polynucleotides of the present invention have further utility in genome mapping, in physical mapping, and in positional cloning of genes. Additionally, the polynucleotide sequences identified as SEQ ID NOS: 1–6, and their variants, may be used to design oligonucleotide probes and primers (referred to collectively as "oligonucleotides"). As detailed below, oligonucleotide probes and primers have sequences that are substantially complementary to the polynucleotide of interest over a certain portion of the polynucleotide. The inventive oligonucleotide probes may be used to detect the presence, and examine the expression patterns, of genes in any organism having sufficiently similar DNA and RNA sequences in their cells using techniques that are well known in the art, such as slot blot DNA hybridization techniques. The inventive oligonucleotide primers may be used for PCR amplifications. Oligonucleotide probes and primers of the present invention may also be used in connection with various microarray technologies, including the microarray technology of Affymetrix, Inc. (Santa Clara, Calif.).

The above-mentioned and additional features of the present invention, together with the manner of obtaining them, will be best understood by reference to the following more detailed description. All references disclosed herein are incorporated herein by reference in their entirety as if each was incorporated individually.

DETAILED DESCRIPTION OF THE INVENTION

In certain aspects, the present invention provides polynucleotides that were isolated by sequencing of cDNA libraries from bovine tissues, including mammary gland cells and paratoid salivary gland cells, together with isolated polypeptides encoded by such polynucleotides. The polynucleotides of the present invention encode polypeptides that show similarities to both histatins and statherins. As discussed above, histatins have been shown to possess toxic activity against a large range of organisms, including oral bacterial and *Candida albicans*. Accordingly, the inventive polypeptides may be employed in the treatment of fungal and bacterial infections of the oral cavity, vagina, urethra, ear, skin, respiratory tract, mucosa and eye, as well in the treatment of systemic infections.

Organisms against which the inventive compositions may be effectively employed include, but are not limited to: *Candida albicans* (both blastospore & mycelial forms), *Actinomyces actonimycetemcomitans, Actinomyces viscosus, Bacteroides forsythus, Bacteroides fragilis, Bacteroides gracilis, Bacteroides ureolyticus, Campylobacter concisus, Campylobacter rectus, Campylobacter showae, Campylobacter sputorum, Capnocytophaga gingivalis, Capnocytophaga ochracea, Capnocytophaga sputigena, Clostridium histolyticum, Eikenella corrodens, Eubacterium nodatum, Fusobacterium nucleatum, Fusobacterium periodonticum, Peptostreptococcus micros, Porphyromonas endodontalis, Porphyromonas gingivalis, Prevotella intermedia, Prevotella nigrescens, Propionibacterium acnes, Pseudomonas aeruginosa, Selenomonas noxia, Staphylcoccus aureus, Streptococcus constellatus, Streptococcus gordonii, Streptococcus intermedius, Streptococcus mutans, Streptococcus oralis, Streptococcus pneumonia, Streptococcus sanguis, Treponema denticola, Treponema pectinvorum, Treptonema socranskii, Veillonella parvula,* and *Wolinella succinogenes.*

The inventive polypeptides may be usefully employed in the treatment of systemic fungal and/or bacterial infections, such as systemic *Candida* infections in individuals who have compromised immune systems. The polypeptides disclosed herein may also be employed in the treatment of dental caries, as well as anti-plaque and anti-tartar agents, and may be delivered by incorporation into toothpastes or mouthwashes. In addition, the inventive polypeptides may be used as anti-microbial agents in cosmetic preparations such as deodorants, soaps, shampoos, etc. Compositions disclosed herein may be used in the treatment of disorders involving infection of the pulmonary region with *Pseudomonas aeruginosa*, including cystic fibrosis. For use in such methods, the compositions may be delivered by a spray mechanism.

The invention polypeptides and polynucleotides may also be employed in veterinary applications, including, but not limited to, treatment of mastitis.

Isolated polynucleotides of the present invention include the polynucleotides identified herein as SEQ ID NOS: 1–6; isolated polynucleotides comprising a polynucleotide sequence selected from the group consisting of SEQ ID NOS: 1–6; isolated polynucleotides comprising at least a specified number of contiguous residues (x-mers) of any of the polynucleotides identified as SEQ ID NOS: 1–6; isolated polynucleotides comprising a polynucleotide sequence that is complementary to any of the above polynucleotides; isolated polynucleotides comprising a polynucleotide sequence that is a reverse sequence or a reverse complement of any of the above polynucleotides; antisense sequences corresponding to any of the above polynucleotides; and variants of any of the above polynucleotides, as that term is described in this specification.

The definition of the terms "complement," "reverse complement," and "reverse sequence," as used herein, is best illustrated by the following example. For the sequence 5' AGGACC 3', the complement, reverse complement, and reverse sequence are as follows:

```
complement              3' TCCTGG 5' reverse complement      3' GGTCCT 5' reverse sequence        5' CCAGGA 3'.
```

Preferably, sequences that are complements of a specifically recited polynucleotide sequence are complementary over the entire length of the specific polynucleotide sequence.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

As used herein, the term "polynucleotide" means a single- or double-stranded polymer of deoxyribonucleotide or ribonucleotide bases and includes DNA and RNA molecules, both sense and anti-sense strands. The term comprehends cDNA, genomic DNA, recombinant DNA, and wholly or partially synthesized nucleic acid molecules. A polynucleotide may consist of an entire gene, or a portion thereof. A gene is a DNA sequence that codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., "Anti-sense techniques," *Methods in Enzymol.* 254(23):363–375, 1995; and Kawasaki et al., *Artific. Organs* 20(8):836–848, 1996.

Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA and protein sequences can be used to amplify and identify genomic and/or cDNA sequences. Synthetic polynucleotides corresponding to the identified sequences, and variants thereof, may be produced by conventional synthesis methods.

All the polynucleotides and polypeptides provided by the present invention are isolated and purified, as those terms are commonly used in the art. Preferably, the inventive polypeptides and polynucleotides are at least about 80% pure, more preferably at least about 90% pure, and most preferably at least about 99% pure.

The polynucleotide sequences identified as SEQ ID NOS: 1–6 were derived from bovine tissue. Certain of the isolated polynucleotides, including those of SEQ ID NO: 1–4 and 6, disclosed herein are full-length sequences in that they contain open reading frames. However, certain of the polynucleotides of the present invention may be "partial" sequences, in that they do not represent a full-length gene encoding a full-length polypeptide. Such partial sequences may be extended by analyzing and sequencing various DNA libraries using primers and/or probes and well known hybridization and/or PCR techniques. Polynucleotide sequences disclosed herein may thus be extended until an open reading frame encoding a polypeptide, a full-length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NOS: 1–6, or a variant thereof, or a portion of one of the sequences of SEQ ID NOS: 1–6, or a variant thereof, when the extended polynucleotide comprises an identified sequence or its variant, or an identified contiguous portion (x-mer) of one of the sequences of SEQ ID NOS: 1–6 or a variant thereof.

The polynucleotides identified as SEQ ID NOS: 1–6 were isolated from bovine cDNA libraries and represent sequences that are expressed in the tissue from which the cDNA was prepared. The sequence information may be used to isolate or synthesize expressible DNA molecules, such as open reading frames or full-length genes, that can then be used as expressible or otherwise functional DNA in cows and other organisms. Similarly, RNA sequences, reverse sequences, complementary sequences, antisense sequences and the like, corresponding to the polynucleotides of the present invention, may be routinely ascertained and obtained using the cDNA sequences identified as SEQ ID NOS: 1–6.

The polynucleotides identified as SEQ ID NOS: 1–6 may contain open reading frames ("ORFs") or partial open reading frames encoding polypeptides. Additionally, open reading frames encoding polypeptides may be identified in extended or full-length sequences corresponding to the sequences set out as SEQ ID NOS: 1–6. Open reading frames may be identified using techniques that are well known in the art. These techniques include, for example, analysis for the location of known start and stop codons, most likely reading frame identification based on codon frequencies, etc. Suitable tools and software for ORF analysis are available, for example, on the Internet at the National Institutes of Health NCBI website. Additional tools and software for ORF analysis are available, and include GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee Tenn. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, polynucleotides and open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including mammalian cells. In vitro expression of polypeptides is also possible, as well known in the art.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

In another aspect, the present invention provides isolated polypeptides encoded, or partially encoded, by the above polynucleotides. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises an isolated polynucleotide sequence or variant provided herein. Polypeptides of the present invention may be naturally purified products, or may be produced partially or wholly using recombinant techniques. Such polypeptides may be glycosylated with bacterial, fungal, mammalian or other eukaryotic carbohydrates or may be non-glycosylated. In specific embodiments, the inventive polypeptides comprise an amino acid sequence encoded by a polynucleotide selected from the group consisting of sequences provided in SEQ ID NOS: 1–6, including the amino acid sequences identified as SEQ ID NO: 7–12, as well as variants of such sequences.

Polypeptides of the present invention may be produced recombinantly by inserting a polynucleotide sequence that encodes the polypeptide into a genetic construct and expressing the polypeptide in an appropriate host. Any of a variety of genetic constructs known to those of ordinary skill in the art may be employed. Expression may be achieved in any appropriate host cell that has been transformed or transfected with a genetic construct containing a polynucleotide that encodes a recombinant polypeptide. Suitable host cells include prokaryotes, yeast, and higher eukaryotic cells. Preferably, the host cells employed are *Escherichia coli*, insect, yeast, or a mammalian cell line such as COS or CHO. The polynucleotide sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence encoded by a polynucleotide of the present invention. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity. Based on similarity to known histatin polypeptides, including, for example, those disclosed in International Patent Publication WO 96/40768, the sequences of SEQ ID NO: 7, 8 and 10 were identified as containing the putative functional motifs, or domains, provided in SEQ ID NO: 13 and 14. Polypeptides containing such functional motifs possess antimicrobial activity.

Functional portions of a polypeptide may also be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2154, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed, site-specific mutagenesis (Kunkel, *Proc. Natl. Acad. Sci. USA* 82:488–492, 1985). Sections of polynucleotide sequence may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, more preferably yet at least 90%, and most preferably at least 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100. By way of example only, assume a queried polynucleotide having 220 nucleic acids has a hit to a polynucleotide sequence in the EMBL database having 520 nucleic acids over a stretch of 23 nucleotides in the alignment produced by the BLASTN algorithm using the default parameters as described below. The 23 nucleotide hit includes 21 identical nucleotides, one gap and one different nucleotide. The percentage identity of the queried polynucleotide to the hit in the EMBL database is thus 21/220 times 100, or 9.5%. The percentage identity of polypeptide sequences may be determined in a similar fashion.

Polynucleotide and polypeptide sequences may be aligned, and percentages of identical residues in a specified region may be determined against another polynucleotide or polypeptide sequence, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The percentage identity of polypeptide sequences may be examined using the BLASTP algorithm. The BLASTN, BLASTP and BLASTX algorithms are available on the NCBI anonymous FTP server under /blast/executables/ and are available from the National Center for Biotechnology Information (NCBI), National Library of Medicine, Building 38A, Room 8N805, Bethesda, Md 20894, USA. The BLASTN algorithm Version 2.0.11 [Jan. 20, 2000], set to the parameters described below, is preferred for use in the determination of polynucleotide variants according to the present invention. The BLASTP algorithm, set to the parameters described below, is preferred for use in the determination of polypeptide variants according to the present invention. The use of the BLAST family of algorithms, including BLASTN, BLASTP and BLASTX, is described in the publication of Altschul, et al., *Nucleic Acids Res.* 25: 3389–3402, 1997.

The FASTA and FASTX algorithms are available on the Internet, and from the University of Virginia by contacting the Vice Provost for Research, University of Virginia, P.O. Box 9025, Charlottesville, Va. 22906-9025, USA. The FASTA algorithm, set to the default parameters described in the documentation and distributed with the algorithm, may be used in the determination of polynucleotide variants. The readme files for FASTA and FASTX Version 1.0 x that are distributed with the algorithms describe the use of the algorithms and describe the default parameters. The use of the FASTA and FASTX algorithms is described in Pearson and Lipman, *Proc. Natl. Acad. Sci. USA* 85:2444–2448, 1988; and Pearson, *Methods in Enzymol.* 183:63–98, 1990.

The following running parameters are preferred for determination of alignments and similarities using BLASTN that contribute to the E values and percentage identity for polynucleotides: Unix running command with the following default parameters: blastall -p blastn -d embldb -e 10 -G 0 -E 0 -r 1 -v 30 -b 30 -i queryseq -o results; and parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence. The BLASTN, FASTA and BLASTP algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt database.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA or BLASTP algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being the same as the polypeptide of the present invention, measured as having an E value of 0.01 or less using the BLASTP algorithm set at the default parameters.

In addition to having a specified percentage identity to an inventive polynucleotide or polypeptide sequence, variant polynucleotides and polypeptides preferably have additional structure and/or functional features in common with the inventive polynucleotide or polypeptide. Polypeptides having a specified degree of identity to a polypeptide of the present invention share a high degree of similarity in their primary structure and have substantially similar functional properties. In addition to sharing a high degree of similarity in their primary structure to polynucleotides of the present invention, polynucleotides having a specified degree of identity to, or capable of hybridizing to, an inventive polynucleotide preferably have at least one of the following features: (i) they contain an open reading frame or partial open reading frame encoding a polypeptide having substantially the same functional properties as the polypeptide encoded by the inventive polynucleotide; or (ii) they contain identifiable domains in common.

In certain embodiments, variant polynucleotides hybridize to a polynucleotide of the present invention under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–6 (or complements, reverse sequences, or reverse complements of those sequences) as a result of conservative substitutions are encompassed within the present invention. Additionally, polynucleotides comprising sequences that differ from the inventive polynucleotide sequences or complements, reverse complements, or reverse sequences as a result of deletions and/or insertions totaling less than 10% of the total sequence length are also contemplated by and encompassed within the present invention. Similarly, polypeptides comprising sequences that differ from the inventive polypeptide sequences as a result of amino acid substitutions, insertions, and/or deletions totaling less than 10% of the total sequence length are contemplated by and encompassed within the present invention, provided the variant polypeptide has similar activity to the inventive polypeptide.

The polynucleotides of the present invention may be isolated from bovine cDNA libraries as described below, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

As noted above, certain of the polynucleotides identified as SEQ ID NOS: 1–6 may be referred to as "partial" sequences, in that they may not represent the full coding portion of a gene encoding a naturally occurring polypeptide. Partial polynucleotide sequences disclosed herein may be employed to obtain the corresponding full-length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene. The present invention thus comprehends isolated polynucleotides comprising a sequence identified in SEQ ID NOS: 1–6, or a variant of one of the specified sequences, that encode a functional polypeptide, including full-length genes. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

As used herein, the term "x-mer," with reference to a specific value of "x," refers to a polynucleotide or polypeptide, respectively, comprising at least a specified number ("x") of contiguous residues of: any of the polynucleotides provided in SEQ ID NOS: 1–6. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NOS: 1–6, or their variants. Polypeptides of the present invention comprehend polypeptides comprising at least a specified number of contiguous residues (x-mers) of any of the polypeptides corresponding to the polynucleotides of SEQ ID NOS: 1–6. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 200-mer, a 220-mer, a 250-mer, a 300-mer, 400-mer, 500-mer or 600-mer of a polynucleotide provided in SEQ ID NOS: 1–6, or a variant of one of the polynucleotides provided in SEQ ID NOS: 1–6. Similarly, polypeptides of the present invention include polypeptides comprising a 20-mer, a 40-mer, a 60-mer, an 80-mer, a 100-mer, a 120-mer, a 150-mer, a 180-mer, a 200-mer, a 220-mer, a 250-mer, a 300-mer, 400-mer, 500-mer or 600-mer of a polypeptide encoded by a polynucleotide provided in SEQ ID NOS: 1–6, or a variant of one of the polynucleotides provided in SEQ ID NOS: 1–6.

The inventive polynucleotides may be isolated by high throughput sequencing of cDNA libraries prepared from bovine tissue as described below in Example 1. Alternatively, oligonucleotide probes and/or primers based on the sequences provided in SEQ ID NOS: 1–6, can be synthesized and used to identify positive clones in either cDNA or genomic DNA libraries from bovine mammary gland cells by means of hybridization or polymerase chain reaction (PCR) techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art (see, for example, Mullis et al., *Cold Spring Harbor Symp. Quant. Biol.*, 51:263, 1987; Erlich, ed., PCR technology, Stockton Press: NY, 1989; and Sambrook et al., in *Molecular cloning: a laboratory manual*, 2nd ed., CSHL Press: Cold Spring Harbor, N.Y., 1989). Positive clones may be analyzed by restriction enzyme digestion, DNA sequencing or the like.

In addition, polynucleotide sequences of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

Oligonucleotide probes and primers complementary to and/or corresponding to SEQ ID NOS: 1–6, and variants of those sequences, are also comprehended by the present invention. Such oligonucleotide probes and primers are substantially complementary to the polynucleotide of interest. An oligonucleotide probe or primer is described as "corresponding to" a polynucleotide of the present invention, including one of the sequences set out as SEQ ID NOS: 1–6 or a variant thereof, if the oligonucleotide probe or primer, or its complement, is contained within one of the sequences set out as SEQ ID NOS: 1–6 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. DNA-DNA hybridization studies may be performed using either genomic DNA or DNA derived by preparing cDNA from the RNA present in the sample.

In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the inventive oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length, or preferably from about 10 to 50 base pairs in length, or more preferably from about 15 to 40 base pairs in length. The probes can be easily selected using procedures well known in the art, taking into account DNA-DNA hybridization stringencies, annealing and melting temperatures, potential for formation of loops, and other factors which are well known in the art. Tools and software suitable for designing probes, and especially suitable for designing PCR primers, are available on the Internet. In addition, a software program suitable for designing probes, and especially for designing PCR primers, is available from Premier Biosoft International, 3786 Corina Way, Palo Alto, Calif. 94303-

4504. Preferred techniques for designing PCR primers are also disclosed in Dieffenbach and Dyksler, PCR *Primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–6.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

Oligonucleotide probes for use in the present invention may be constructed synthetically prior to immobilization on an array, using techniques well known in the art (See, for example, Gait, ed., *Oligonucleotide synthesis a practical approach*, IRL Press: Oxford, England, 1984). Automated equipment for the synthesis of oligonucleotides is available commercially from such companies as Perkin Elmer/Applied Biosystems Division (Foster City, Calif.) and may be operated according to the manufacturer's instructions. Alternatively, the probes may be constructed directly on the surface of the array using techniques taught, for example, in PCT Publication No. WO 95/00530.

The solid substrate and the surface thereof preferably form a rigid support and are generally formed from the same material. Examples of materials from which the solid substrate may be constructed include polymers, plastics, resins, membranes, polysaccharides, silica or silica-based materials, carbon, metals and inorganic glasses. Synthetically prepared probes may be immobilized on the surface of the solid substrate using techniques well known in the art, such as those disclosed in U.S. Pat. No. 5,412,087.

In one such technique, compounds having protected functional groups, such as thiols protected with photochemically removable protecting groups, are attached to the surface of the substrate. Selected regions of the surface are then irradiated with a light source, preferably a laser, to provide reactive thiol groups. This irradiation step is generally performed using a mask having apertures at predefined locations using photolithographic techniques well known in the art of semiconductors. The reactive thiol groups are then incubated with the oligonucleotide probe to be immobilized. The precise conditions for incubation, such as temperature, time and pH, depend on the specific probe and can be easily determined by one of skill in the art. The surface of the substrate is washed free of unbound probe and the irradiation step is repeated using a second mask having a different pattern of apertures. The surface is subsequently incubated with a second, different, probe. Each oligonucleotide probe is typically immobilized in a discrete area of less than about 1 mm$^2$. Preferably each discrete area is less than about 10,000 mm$^2$, more preferably less than about 100 mm$^2$. In this manner, a multitude of oligonucleotide probes may be immobilized at predefined locations on the array.

The resulting array may be employed to screen for differences in organisms or samples or products containing genetic material as follows. Genomic or cDNA libraries are prepared using techniques well known in the art. The resulting target DNA is then labeled with a suitable marker, such as a radiolabel, chromophore, fluorophore or chemiluminescent agent, using protocols well known for those skilled in the art. A solution of the labeled target DNA is contacted with the surface of the array and incubated for a suitable period of time.

The surface of the array is then washed free of unbound target DNA and the probes to which the target DNA hybridized are determined by identifying those regions of the array to which the markers are attached. When the marker is a radiolabel, such as $^{32}$P, autoradiography is employed as the detection method. In one embodiment, the marker is a fluorophore, such as fluorescein, and the location of bound target DNA is determined by means of fluorescence spectroscopy. Automated equipment for use in fluorescence scanning of oligonucleotide probe arrays is available from Affymetrix, Inc. (Santa Clara, Calif.) and may be operated according to the manufacturer's instructions. Such equipment may be employed to determine the intensity of fluorescence at each predefined location on the array, thereby providing a measure of the amount of target DNA bound at each location. Such an assay would be able to indicate not only the absence and presence of the marker probe in the target, but also the quantitative amount as well.

In this manner, oligonucleotide probe kits of the present invention may be employed to examine the presence/absence (or relative amounts in case of mixtures) of polynucleotides in different biological samples, or products containing different materials, rapidly and in a cost-effective manner.

Another aspect of the present invention involves collections of a plurality of polynucleotides of the present invention. A collection of a plurality of the polynucleotides of the present invention, particularly the polynucleotides identified as SEQ ID NOS: 1–6, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–6. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–6, including variants of those polynucleotides.

In another aspect, the present invention provides genetic constructs comprising, in the 5'–3' direction, a gene promoter sequence and an open reading frame coding for at least a functional portion of a polypeptide encoded by a polynucleotide of the present invention. In certain embodiments, the genetic constructs of the present invention also comprise a gene termination sequence. The open reading frame may be oriented in either a sense or antisense direction. Genetic constructs comprising a non-coding region of a gene coding for a polypeptide encoded by the above polynucleotides or a nucleotide sequence complementary to a non-coding region, together with a gene promoter sequence, are also provided. A terminator sequence may form part of this construct. Preferably, the gene promoter and termination sequences are functional in a host organism. More preferably, the gene promoter and termination sequences are common to those of the polynucleotide being introduced. The genetic construct may further include a marker for the identification of transformed cells.

Techniques for operatively linking the components of the genetic constructs are well known in the art and include the use of synthetic linkers containing one or more restriction endonuclease sites as described, for example, by Sambrook et al., in *Molecular cloning: a laboratory manual*, Cold Spring Harbor Laboratories Press: Cold Spring Harbor, N.Y., 1989. The genetic constructs of the present invention may be linked to a vector having at least one replication system, for example, *E. coli*, whereby after each manipulation, the resulting construct can be cloned and sequenced and the correctness of the manipulation determined.

Transgenic cells comprising the genetic constructs of the present invention are also provided by the present invention, together with organisms comprising such transgenic cells, products and progeny of such organisms. Techniques for stably incorporating genetic constructs into the genome of target organisms are well known in the art.

In one aspect, the present invention provides methods for using one or more of the inventive polypeptides or polynucleotides to treat disorders in a subject, preferably a mammal, including, but not limited to, humans and cows. In this aspect, the polypeptide or polynucleotide is generally present within a composition additionally comprising a physiologically acceptable carrier.

Preferred routes of administration for the inventive compositions, will vary depending on the site and type of disorder to be treated. For example, either systemic or local administration may be preferred. In general, the compositions may be administered by injection (e.g., intradermal, intramuscular, intravenous, or subcutaneous); intranasally (e.g., by aspiration); orally; or topically. Similarly, the preferred frequency of administration and dosage will vary from individual to individual, and can be readily determined by one of skill in the art using standard techniques. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 $\mu$g per kg of host. Suitable dose sizes will vary with the size of the mammal, but will typically range from about 0.1 ml to about 5 ml.

While any suitable carrier known to those of ordinary skill in the art may be employed in the compositions of this invention, the preferred type of carrier will vary depending on the mode of administration. For parenteral administration, such as subcutaneous injection, the carrier preferably comprises water, saline, alcohol, a lipid, a wax, or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. The compositions of the present invention may include additional components, such as anti-inflammatory agents and known anti-bacterial agents. When used as anti-microbial cosmetic compositions, the inventive compositions may contain, for example, binders and thickeners, flavors and/or perfumes as taught in U.S. Pat. No. 5,672,351.

A composition of the present invention may contain a polynucleotide encoding one or more polypeptides as described above, such that the polypeptide is generated in situ. In such compositions, the polynucleotide may be present within any of a variety of delivery systems known to those of ordinary skill in the art, including nucleic acid expression systems, and bacterial and viral expression systems. Appropriate nucleic acid expression systems contain the necessary polynucleotide sequences for expression in a mammal (such as a suitable promoter and terminator signal). Bacterial delivery systems involve the administration of a bacterium (such as *Bacillus* Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating polynucleotides into such expression systems are well known in the art. The DNA may also be "naked," as described, for example, in Ulmer etal., *Science* 259:1745–1749, 1993; and reviewed by Cohen, *Science* 259:1691–1692, 1993. The uptake of naked DNA may be increased by coating the DNA onto biodegradable beads, which are efficiently transported into the cells.

In certain embodiments, the inventive compositions comprise a polypeptide or polynucleotide disclosed herein in combination with an immunostimulant, such as an adjuvant. Any of a variety of immunostimulants may be employed in such compositions to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis*, or *Mycobacterium tuberculosis*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A, and Quil A.

The polypeptides of the present invention may additionally be used in assays to determine biological activity, to raise antibodies, to isolate corresponding ligands or receptors, and in assays to quantitatively determine levels of protein or cognate corresponding ligand or receptor, as anti-inflammatory agents.

The polynucleotides of the present invention may be used for expression in a transgenic animal, as disclosed in U.S. Pat. No. 5,714,345, which teaches the use of transgenic animals capable of expressing a desired protein prepared by introducing into an egg or embryo cell of an animal, an expression construct containing the sequence corresponding at least in part to a specific polynucleotide, which encodes the desired protein. In the same manner, the desired protein corresponding to a selected polynucleotide sequence of the present invention, may be employed in transgenic animals for the production of milk containing the desired protein, as disclosed in U.S. Pat. No. 5,849,992.

In addition, the regulatory sequences contained in the inventive polynucleotide sequences, or regulatory sequences isolated using the inventive sequences for genome screening and sequencing, as well known in the art, may be used in transgenic animals to direct the expression of a desired gene product according to the nature of the regulatory polynucleotide sequence, in a way similar to that taught in U.S. Pat. No. 5,850,000.

EXAMPLE 1

Isolation of cDNA Sequences from Bovine cDNA Libraries

Polynucleotides were isolated from bovine mammary gland and paratoid salivary gland cDNA libraries, from a normalized bovine embryo cDNA library and from a normalized bovine library as follows.

Bovine mammary gland cDNA expression libraries were constructed and screened as follows. mRNA was extracted from lactating bovine mammary tissue (late lactating, non-pregnant Jersey, 2 hours post-milking) using standard protocols. mRNA was precipitated with ethanol and the total RNA preparate was purified using a Poly(A) Quik MRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. cDNA expression libraries were prepared from bovine paratoid salivary gland tissue and from bovine embryo tissue essentially as described above. In addition, a normalized cDNA expression library (referred to as the normalized bovine library) was prepared from a pool of bovine embryo, immunological, placental and mammary tissue, also essentially as described above.

The resulting cDNAs were packaged using a Gigapack II Packaging Extract (Stratagene) employing 1 μl of sample DNA from the 5 μl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactoside (X-gal) and isopropylthio-beta-galactoside (IPTG).

Of the colonies plated and picked for DNA preparations, the large majority contained an insert suitable for sequencing. Positive colonies were cultured in NZY broth with kanamycin and cDNA was purified by means of REAL DNA minipreps (Qiagen, Venlo, The Netherlands). Agarose gel at 1% was used to screen sequencing templates for chromosomal contamination. Dye terminator sequences were prepared using a Biomek 2000 robot (Beckman Coulter Inc., Fullerton, Calif.) for liquid handling and DNA amplification using a 9700 PCR machine (Perkin Elmer/Applied Biosystems, Foster City, Calif.) according to the manufacturer's protocol.

The DNA sequences for positive clones were obtained using a Perkin Elmer/Applied Biosystems Division Prism 377 sequencer. cDNA clones were sequenced from the 5' end. The sequences of polynucleotides isolated from mammary gland cDNA libraries are identified as SEQ ID NOS: 1 and 6. The cDNA sequence identified as SEQ ID NO: 2 was isolated from the normalized bovine library, with the sequence of SEQ ID NO: 3 being isolated from the normalized bovine embryo library, and the sequences of SEQ ID NO: 4 and 5 being isolated from the paratoid salivary gland library. Amino acid sequences corresponding to the cDNA sequences of SEQ ID NO: 1–6 are provided in SEQ ID NO: 7–12, respectively.

Based on homology to known sequences, the polynucleotide sequences of SEQ ID NO: 1–6 were identified as encoding bovine histatins. All these sequences have similar N-termini but different C-termini. In addition, the amino acid sequence encoded by the DNA sequence of SEQ ID NO: 4 is identical to that encoded by SEQ ID NO: 1, but the two DNA sequences differ in their 5' untranslated regions. A putative functional histatin anti-microbial domain is present in the amino acid sequences of SEQ ID NO: 7, 8 and 10 at residues 31–38 (Lys-Lys-His-His-Arg-Lys-Tyr-Phe; (SEQ ID NO: 14). This domain differs from that of the corresponding human histatin homologue in that it contains an extra amino acid. In addition, the sequences of SEQ ID NO: 7, 8 and 10 contain a stratherin-like phosphorylation site about ten amino acids upstream towards the N-terminus. This stratherin motif is not present in the previously identified human and macaque histatin molecules. Using standard Northern techniques and 14 different bovine tissues, expression of the bovine histatin disclosed herein was observed only in mammary and parotid salivary tissue.

BLASTN Polynucleotide Analysis

The isolated cDNA sequences were compared to sequences in the EMBL DNA database using the computer algorithm BLASTN. Comparisons of DNA sequences provided in SEQ ID NOS: 1–6 to sequences in the EMBL DNA database (using BLASTN) were made as of December 2001, using Version 2.0.11 [Jan. 20, 2000], and the following Unix runing command: blastall -p blastn -d embldb -e 10 -G0-E0-r 1 -v 30 -b 30-i queryseq -o.

The sequences of SEQ ID NOS: 1–6 were determined to have less than 50% identity, determined as described above, to sequences in the EMBL database using the computer algorithm BLASTN, as described above.

BLASTP Polypeptide Analysis

The isolated polypeptide sequences were compared to sequences in the SwissProt protein database using the computer algorithm BLASTP. Comparisons of polypeptide sequences provided in SEQ ID NOS: 7–12 to sequences in the SwissProt protein database (using BLASTP) were made as of December 2001, using Version 2.0.11 [Jan. 20, 2000], and the following Unix running command: blastall -p blastn -d embldb -e 10 -G0-E0-v 30 -b 30 -i queryseq -o. The sequences of SEQ ID NOS: 7–12 were determined to have less than 50% identity, determined as described above, to sequences in the SwissProt protein database.

BLASTX Polynucleotide Analysis

The isolated CDNA sequences were compared to sequences in the SwissProt protein database using the computer algorithm BLASTX. Specifically, comparisons of DNA sequences provided in SEQ ID NOS: 1–6 to sequences in the SwissProt protein database (using BLASTP) were made as of December 2001, using Version 2.0.11 [Jan. 20, 2000], and the following Unix running command: blastall -p blast -d embldb -e 10 -G0-E0-v 30 -b 30 -i queryseq -o. The sequences of SEQ ID NOS: 1–6 were determined to have less than 50% identity, determined as described above, to sequences in the SwissProt protein using the computer algorithm BLASTX, as described above.

EXAMPLE 2

Expression of mRNA in Bovine Mammary Tissue

This example illustrates the determination of mRNA expression levels of mammary-gland specific sequences, isolated essentially as described in Example 1, in biological samples.

RNA was extracted from mammary gland tissue obtained from a non-pregnant heifer, a pregnant cow and a lactating cow, as well as from bovine liver, forebrain and kidney, using TRIzol (Gibco BRL, Gaithersburg, Md.) following the manufacturer's protocol. Sets of the various total RNA samples were run on 1.2% agarose/formaldehyde gels, 5 µg/lane. Following transfer to nitrocellulose membranes, RNA was cross-linked with ultraviolet light.

DNA probes were prepared from bacterial clones transformed with cDNA corresponding to SEQ ID NO: 15 by excision of the insert of the cDNA clone using EcoRI and XhoI restriction endonucleases, or by PCR amplification of the insert of the cDNA clone using T7 and T3 primers (Gibco BRL), or by using the entire cDNA clone. Probes were radiolabeled with $\alpha$-$P^{32}$-dCTP using Rediprime DNA labeling kits (Amersham Pharmacia Biotech, Uppsala, Sweden). SEQ ID NO: 15 is contained within the sequence of SEQ ID NO: 1.

Blots were hybridized overnight with rotation at 65° C. in a buffer containing 10–20 ml of 500 mM $NaH_2PO_4$, 1 mM EDTA, 7% SDS, and then washed for 15 minutes at 65° C., first in 2×SSC/0.1% and then in 0.2×SSC/0.1% SDS. The blots were exposed to Kodak XAR X-ray film for appropriate times.

The insert of the cDNA clone corresponding to the polynucleotide sequence of SEQ ID NO: 15 hybridized strongly with a transcript of approximately 0.8 kb in the lactating mammary gland sample. Very weak hybridization to transcripts of a similar size was detected in the mammary samples from a non-pregnant heifer and a pregnant non-lactating cow. No transcripts could be detected in the other tissue samples.

SEQ ID NOS: 1–15 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polypeptide encoded by SEQ ID NO: 4, wherein the polypeptide has histatin activity.

2. An isolated polypeptide comprising SEQ ID NO: 10.

3. A composition comprising a polypeptide according to claim 2, and at least one component selected from the group consisting of: physiologically acceptable carriers and immunostimulants.

4. A composition according to claim 3, wherein the composition is a cosmetic composition.

5. An isolated polypeptide comprising an amino acid sequence selected from the group consisting of:
   (a) sequences having at least 75% identity to SEQ ID NO: 10;
   (b) sequences having at least 90% identity to SEQ ID NO: 10; and
   (c) sequences having at least 95% identity to SEQ ID NO: 10, wherein the polypeptide has substantially the same functional activity as SEQ ID NO: 10.

6. A composition comprising a polypeptide according to claim 5, and at least one component selected from the group consisting of: physiologically acceptable carriers and immunostimulants.

7. A composition according to claim 6, wherein the composition is a cosmetic composition.

* * * * *